(12) United States Patent
Matsushita et al.

(10) Patent No.: US 9,962,439 B2
(45) Date of Patent: May 8, 2018

(54) INJECTABLE VACCINE COMPOSITION

(71) Applicant: NITTO DENKO CORPORATION, Osaka (JP)

(72) Inventors: Kyohei Matsushita, Osaka (JP); Masahiro Fukasaka, Osaka (JP); Arimichi Okazaki, Osaka (JP); Eiji Kiyotoh, Osaka (JP); Katsuyuki Okubo, Osaka (JP); Daisuke Asari, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days. days.

(21) Appl. No.: 14/916,807

(22) PCT Filed: Oct. 2, 2014

(86) PCT No.: PCT/JP2014/076351
§ 371 (c)(1),
(2) Date: Mar. 4, 2016

(87) PCT Pub. No.: WO2015/050181
PCT Pub. Date: Apr. 9, 2015

(65) Prior Publication Data
US 2016/0287697 A1    Oct. 6, 2016

(30) Foreign Application Priority Data
Oct. 3, 2013  (JP) ................. 2013-208662

(51) Int. Cl.
A61K 39/00   (2006.01)
A61K 39/39   (2006.01)
A61K 9/00    (2006.01)

(52) U.S. Cl.
CPC ............ *A61K 39/39* (2013.01); *A61K 9/0019* (2013.01); *A61K 39/00* (2013.01); *A61K 2039/55572* (2013.01)

(58) Field of Classification Search
CPC ................ A61K 39/00; A61K 39/02
USPC .......... 424/184.1, 234.1, 278.1, 282.1, 283.1
See application file for complete search history.

(56) References Cited

U.S. PATENT DOCUMENTS

| | | |
|---|---|---|
| 6,440,426 B1 | 8/2002 | Wheeler et al. |
| 2005/0152919 A1 | 7/2005 | Ward et al. |
| 2008/0171079 A1 | 7/2008 | Hanon et al. |
| 2008/0279926 A1 | 11/2008 | Vandepapeliere |
| 2010/0312045 A1 | 12/2010 | Ramlov et al. |
| 2011/0045059 A1 | 2/2011 | Hanon et al. |
| 2011/0104260 A1 | 5/2011 | Hanon et al. |

FOREIGN PATENT DOCUMENTS

| | | |
|---|---|---|
| JP | H08-245702 A | 9/1996 |
| JP | 2000-103745 A | 4/2000 |
| JP | 4043533 B2 | 2/2008 |
| JP | 2009-242367 A | 10/2009 |
| JP | 2012-82156 A | 4/2012 |
| WO | 96/23002 A1 | 8/1996 |
| WO | 2005/027964 A1 | 3/2005 |
| WO | 2006/094756 A2 | 9/2006 |
| WO | 2007/068907 A2 | 6/2007 |
| WO | 2009/065415 A1 | 5/2009 |
| WO | 2013/006569 A2 | 1/2013 |

OTHER PUBLICATIONS

Marjatta Nurminen et al., "The role of the O antigen in adjuvant activity of lipopolysaccharide", FEMS Microbiology Letters, 1991, pp. 51-54, vol. 83, No. 1.
International Search Report issued with respect to application No. PCT/JP2014/076351, dated Dec. 16, 2014.
International Preliminary Report on Patentability issued with respect to application No. PCT/JP2014/076351, dated Apr. 5, 2016.
Mulyatno et al., "Mucosal adjuvanticity of bacterial lipopolysaccharide in compared with cholera toxin", Proceedings of the Japanese Society for Immunology, vol. 41, 2012, pp. 89.
Dawei et al., Journal of Dental Health, "Micromolar Fluoride Reduces Alveolar Bone Loss in Experimental Rat Periodontitis", vol. 62, No. 2, 2012.
European Search Report issued with respect to Application No. 14850351.9, dated Mar. 22, 2017.
Revised European Search Report issued with respect to Application No. 14850351.9, dated May 12, 2017.
Office Action issued with respect to European Application No. 14850351.9, dated Dec. 21, 2017.
Arenas et al., "The Role of Bacterial Lipopolysaccharides as Immune Modulator in Vaccine and Drug Development", Endocrine, Metabolic & Immune Disorders—Drug Targets, 2012, 12(3):221-235.

*Primary Examiner* — Rodney P Swartz
(74) *Attorney, Agent, or Firm* — Greenblum & Bernstein, P.L.C.

(57) ABSTRACT

The present invention aims at providing an injectable vaccine composition that is safe, useful as a prophylactic or therapeutic agent for cancers or infectious diseases, and capable of inducing the systemic immune response safely and effectively. The present invention is an injectable vaccine composition to be administered by injection to a human being or an animal, containing: at least one antigen, and as an adjuvant, a lipopolysaccharide derived from at least one gram negative bacterium selected from the group consisting of *Serratia, Leclercia, Rahnella, Acidicaldus, Acidiphilium, Acidisphaera, Acidocella, Acidomonas, Asaia, Belnapia*, Craurococcus, *Gluconacetobacter, Gluconobacter, Kozakia, Leahibacter*, Muricoccus, *Neoasaia, Oleomonas*, Paracraurococcus, *Rhodopila*, Roseococcus, *Rubritepida, Saccharibacter*, Stella, Swaminathania, Teichococcus, *Zavarzinia, Pseudomonas, Achromobacter, Bacillus, Methanoculleus, Methanosarcina, Clostridium*, Micrococcus, *Flavobacterium, Pantoea, Acetobacter, Zymomonas, Xanthomonas*, and *Enterobacter*, or a salt thereof.

2 Claims, 7 Drawing Sheets

INJECTABLE VACCINE COMPOSITION

SEQUENCE LISTING

The instant application contains a Sequence Listing which has been submitted electronically in ASCII format and is hereby incorporated by reference in its entirety. Said ASCII copy, created on Apr. 21, 2016, is named P49399_SL.txt and is 1,866 bytes in size.

TECHNICAL FIELD

The present invention relates to an injectable vaccine composition that is useful as a prophylactic or therapeutic agent for cancers or infectious diseases. In particular, the present invention relates to an injectable vaccine composition containing a specific lipopolysaccharide as an adjuvant, that is capable of inducing the systemic immune response safely and effectively by being administered together with an antigen.

BACKGROUND ART

As the dosage form of vaccine preparations, most of the commercial products that are currently available are injections.

Existing vaccine preparations, for example, common influenza vaccine preparations that are used in Japan do not contain an adjuvant, and the effect thereof is not sufficient. There is also a case where the condition of a patient infected with influenza becomes serious even though the patient has received such a vaccine preparation.

Also, there exists a human papillomavirus vaccine product containing monophosphoryl lipid as an adjuvant. However, it is the actual circumstance that the monophosphoryl lipid is obtained by removing a sugar chain part of a lipopolysaccharide derived from *Salmonella typhimurium* for improving the safety, and thus the effect as an adjuvant is attenuated.

Therefore, an adjuvant containing a lipopolysaccharide derived from a bacterial species that is relatively safe and capable of achieving both high safety and the effect of stimulating immunity has been strongly demanded.

For example, Patent Literature 1 proposes a lipopolysaccharide (LPS) derived from *Pantoea* bacteria, and describes that the LPS is safer than conventional LPSs, and the immune reaction is enhanced when it is administered together with an antigen.

Patent Literature 1, however, lacks distinct reference and illustration regarding the use for acquired immunity, and also lacks reference to the optimum ratio of adjuvant/antigen.

Also, for example, Patent Literature 2 proposes a vaccine containing a combination of Poly(I:C) and zymosan as an inactivated antigen of a pathogen, and an immunostimulant (adjuvant), and describes an example of using a lipopolysaccharide (LPS) derived from *Pantoea agglomerans* as an adjuvant, and an influenza virus as a pathogen.

In the example of the vaccine containing a lipopolysaccharide (LPS) derived from *Pantoea agglomerans* described in Patent Literature 2, the vaccine is administered to a nasal mucous membrane, and there is no teaching about injection administration. Generally, it is the common knowledge in the art that the effective adjuvant differs depending on the administration site. Therefore, it is unclear whether a lipopolysaccharide (LPS) derived from *Pantoea agglomerans* is effective by injection administration from the example of the vaccine containing a lipopolysaccharide (LPS) derived from *Pantoea agglomerans* described in Patent Literature 2.

CITATION LIST

Patent Literatures

Patent Literature 1: Japanese Patent No. 4043533
Patent Literature 2: JP 2009-242367 A

SUMMARY OF INVENTION

Technical Problem

In view of the aforementioned situation, it is an object of the present invention to provide an injectable vaccine composition that is safe, useful as a prophylactic or therapeutic agent for cancers or infectious diseases, and capable of effectively inducing the systemic immune response.

Solution to Problem

The present inventors made various investigations for solving the aforementioned problem, and found that it is possible to induce the systemic immune response safely and effectively by injection administration using, as an adjuvant, a lipopolysaccharide derived from at least one gram negative bacterium selected from the group consisting of *Serratia, Leclercia, Rahnella, Acidicaldus, Acidiphilium, Acidisphaera, Acidocella, Acidomonas, Asaia, Belnapia,* Craurococcus, *Gluconacetobacter, Gluconobacter, Kozakia, Leahibacter,* Muricoccus, *Neoasaia, Oleomonas,* Paracraurococcus, *Rhodopila,* Roseococcus, *Rubritepida, Saccharibacter, Stella, Swaminathania,* Teichococcus, *Zavarzinia, Pseudomonas, Achromobacter, Bacillus, Methanoculleus, Methanosarcina, Clostridium,* Micrococcus, *Flavobacterium, Pantoea, Acetobacter, Zymomonas, Xanthomonas,* and *Enterobacter,* or a salt thereof, together with an antigen. These findings have now led to completion of the present invention.

That is, the present invention is an injectable vaccine composition to be administered by injection to a human being or an animal, containing at least one antigen, and as an adjuvant, a lipopolysaccharide derived from at least one gram negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas,* and *Enterobacter,* or a salt thereof.

In the injectable vaccine composition of the present invention, a mass ratio between the adjuvant and the antigen (total mass of the adjuvant/total mass of the antigen) is preferably 0.002 to 50.

The injectable vaccine composition of the present invention is preferably used for inducing humoral immunity.

In the injectable vaccine composition of the present invention, the antigen is preferably an antigen derived from an infectious disease or a cancer antigen.

Hereinafter, the present invention will be specifically described.

The injectable vaccine composition of the present invention contains at least one antigen and an adjuvant.

In the injectable vaccine composition of the present invention, the mass ratio between the adjuvant and the antigen (total mass of the adjuvant/total mass of the antigen) is preferably 0.002 to 50. If the mass is less than 0.002, the immunity of sufficient strength may not be induced, whereas if it is more than 50, a safety problem may arise in the injectable vaccine composition of the present invention. A more preferred lower limit of the mass ratio between the adjuvant and the antigen is 0.01, and a more preferred upper limit thereof is 10. By selecting the mass ratio between the adjuvant and the antigen within this range, it is possible to induce the immunity of sufficient strength while ensuring the safety.

The "mass of the antigen" used herein refers to the mass of the antigen protein or peptide contained in the antigen in the vaccine unless otherwise specified. Therefore, when the antigen is a substance derived from an organism such as a virus, the wording means the mass of the whole protein contained in the antigen.

The antigen used in the present invention may be an antigen derived from an infectious disease, and non-limiting examples of the antigen derived from an infectious disease include infectious pathogens and antigens derived from infectious pathogens.

Non-limiting examples of the diseases developed by an infectious pathogen include viral diseases such as diseases developed by infection with a virus such as an adenovirus, a herpesvirus (e.g., HSV-I, HSV-II, CMV, or VZV), a poxvirus (e.g., smallpox or vaccinia, or an orthopoxvirus such as molluscum contagiosum), a picornavirus (e.g., a rhinovirus or an enterovirus), an orthomyxovirus (e.g., an influenza virus), a paramyxovirus (e.g., a parainfluenza virus, a mumps virus, a measles virus, or a respiratory syncytial virus (RSV)), a coronavirus (e.g., SARS), a papovavirus (for example, a human papilloma virus that causes genital wart, bladder wart vulgaris, or plantar wart), a hepadnavirus (e.g., a hepatitis B virus), a flavivirus (e.g., a hepatitis C virus or a dengue virus), or a retrovirus (e.g., a lentivirus such as HIV), bacterial diseases such as diseases developed by infection with a bacterium such as *Escherichia, Enterobacter, Salmonella, staphylococcus*, dysentery bacilli, *Listeria, Aerobacter, helicobacter, Klebsiella, Proteus, Pseudomonas, streptococcus, Chlamydia, mycoplasma*, pneumococcus, *Neisseria, Clostridium, bacillus, Corynebacterium, mycobacterium, Campylobacter, Vibrio Vibrio, Serratia, Providencia, Chromobacterium, Brucella, Yersinia, Haemophilus*, or *Bordetella*, fungous diseases including, but not limited to, *Chlamydia*, candidiasis, aspergillosis, histoplasmosis, and cryptococcal meningitis, malaria, *Pneumocystis carinii* pneumonia, leishmaniasis, cryptosporidiosis, toxoplasmosis, and *Trypanosoma* infection.

In the present invention, the antigen derived from an infectious disease is preferably at least one selected from the group consisting of an antigen derived from an influenza virus, an antigen derived from human papillomavirus, and an antigen derived from pneumococcus, with an antigen derived from an influenza virus being more preferred.

Here, the influenza virus is an RNA envelope virus belonging to Orthomyxoviridae, and having a particle size of about 100 nm in diameter, and is classified into types A, B and C based on the antigenicity of the internal protein. The influenza virus is composed of a core of ribonucleic acid (RNA) associated with an internal nucleocapsid surrounded by a virus envelope having a lipid bilayer structure or nucleic protein, and an external glycoprotein. The inner layer of the virus envelope is mainly formed of matrix protein, and the outer layer is mostly formed of a lipid substance derived from the host. RNA of the influenza virus has a multipartite structure. Influenza that is pandemic all over the world is caused by an influenza A type virus, and the influenza A type virus has two envelope glycoproteins: hemagglutinin (HA) and neuraminidase (NA), and is classified into 16 subtypes for HA and 9 subtypes for NA depending on the antigenicity.

In the present invention, as the antigen derived from an infectious disease, antigens derived from influenza A type and B type viruses are preferably used. The subtype of the influenza A type and B type viruses is not particularly limited, and may be a subtype that is already isolated, or a subtype that will be isolated in future.

In the present invention, the antigen derived from an influenza virus is not particularly limited as long as it is at least part of various components constituting the influenza virus, and may be a subvirion obtained by digesting a purified viral particle with an organic solvent/surfactant or another reagent so that the lipid envelope is solubilized, or a viral subunit such as HA and NA, or may be a viral whole particle. From the view point of immunogenicity, HA or a viral whole particle is preferred. The viral whole particle is preferably inactivated with formalin or the like.

The method for preparing the aforementioned influenza viral antigen is not particularly limited, and any known method can be used without restriction. One exemplary method includes: infecting a hen egg with a viral strain that is isolated from an animal or a patient infected with influenza, culturing the hen egg by an ordinary method, and preparing an antigen from the purified undiluted viral culture. Also an antigen derived from a virus prepared in cultured cells by genetic engineering may be used.

The antigen used in the present invention may be a cancer antigen. Non-limiting examples of the cancer antigen include cancer antigen peptides, cancer antigen proteins, and cancer cell lysates and extracts that are products based on genes listed below. The term cancer used herein means cancers associated with abnormal expression, for example, overexpression of a cancer gene, e.g., hematopoietic organ tumors and solid cancers.

Examples of the cancer gene include survivin gene, GPC3 gene, HER2/neu gene, MAGE3 gene, MAGE A1 gene, MAGE A3/A6 gene, MAGE A4 gene, MAGE12 gene, proteinase-3 gene, AFP gene, CA-125 gene, CD44 gene, CEA gene, c-Kit gene, c-met gene, c-myc gene, L-myc gene, COX2 gene, CyclinD1 gene, Cytokeratin-7 gene, Cytokeratin-19 gene, Cytokeratin-20 gene, E2F1 gene, E2F3 gene, EGFR gene, Gli1 gene, hCGβ gene, HIF-1α gene, HnRNP A2/B1 gene, hTERT gene, MDM gene, MDR-1 gene, MMP-2 gene, MMP-9 gene, Muc-1 gene, Muc-4 gene, Muc-7 gene, NSE gene, ProGRP gene, PSA gene, RCAS1 gene, SCC gene, thymoglobulin gene, VEGF-A gene and VEGF-A gene. Non-limiting examples of the cancer associated with abnormal expression of survivin gene include malignant lymphoma, bladder cancer, lung cancer, and colon cancer. Non-limiting examples of the cancer associated with abnormal expression of GPC3 gene include hepatic cancer, bile duct cancer, and stomach cancer. Non-limiting examples of the cancer associated with abnormal expression of HER2/neu gene include breast cancer, stomach cancer, ovarian cancer, uterine cancer, bladder cancer, non-small cell lung cancer, and prostatic cancer. Non-limiting examples of the cancer associated with abnormal expression of MAGE3 gene include melanoma, lung cancer, head and neck cancer, bladder cancer, stomach cancer, esophageal cancer, and liver cancer. Non-limiting examples of the cancer associated with abnormal expression of proteinase-3 gene include acute myelogenous leukemia and pancreatic cancer. Regarding a cancer that is caused by a virus, the gene derived from the virus is regarded as the cancer gene. Non-limiting examples thereof include IPEP87 peptide that is a peptide derived from hepatitis C virus (HCV) protein, and HBVenv peptide that is a peptide derived from hepatitis B virus (HBV) protein.

In the present invention, the cancer antigen is preferably an endogenous or synthetic cancer antigen peptide selected from the group consisting of survivin 2B peptide and/or modified survivin 2B peptide, IPEP87 peptide and/or modified IPEP87 peptide, HBVenv peptide and/or modified HBVenv peptide, HER2/neu_E75 peptide and/or modified HER2/neu_E75 peptide, GPC3 peptide and/or modified GPC3 peptide, HER2/neu_A24 peptide and/or modified HER2/neu_A24 peptide, MAGE3_A24 peptide and/or modified MAGE3_A24 peptide, PR1 peptide and/or modified PR1 peptide, HER2/neu_A02 peptide and/or modified HER2/neu_A02 peptide, MAGE3_A02 peptide and/or modified MAGE3_A02 peptide, and MUC1 peptide and/or modified MUC1 peptide. The term "modified XX peptide" (XX is the name of an arbitrary peptide) used herein means a modified peptide in which all or part of amino acids in the XX peptide are modified by substitution, modification or the like.

Examples of the modified XX peptide include:
(a) peptides having an amino acid sequence in which one to several amino acids, for example, one, two, three, four or five amino acids are substituted, deleted or added in the amino acid sequence of the XX peptide; and
(b) peptides having an amino acid sequence in which all or part of amino acids, for example, one or a plurality of, for example, one, two, three, four, five, six, seven, eight, nine or ten amino acids are modified in the amino acid sequence of the XX peptide.

Non-limiting examples of the "modification" of amino acid that can be involved in the modified XX peptide include acetylation, alkylation such as methylation, glycosylation, hydroxylation, carboxylation, aldehydation, phosphorylation, sulfonylation, formylation, aliphatic chain additional modification such as myristoylation, palmitoylation or stearoylation, octanoylation, esterification, amidation, deamidation, disulfide bond forming modification such as cystine modification, glutathione modification or thioglycollic acid modification, saccharification, ubiquitination, succinimide formation, glutamylation, and prenylation.

The modified XX peptide may involve a combination of substitution, deletion or addition of one or more amino acids, with modification of one or more amino acids.

The term "survivin 2B peptide" used herein means a peptide derived from a cancer gene product survivin, having a sequence of Ala Tyr Ala Cys Asn Thr Ser Thr Leu (SEQ ID NO: 1).

The term "GPC3 peptide" used herein means a peptide derived from a cancer gene product GPC3, having a sequence of Glu Tyr Ile Leu Ser Leu Glu Glu Leu (SEQ ID NO: 2).

The term "HER2/neu_A24 peptide" used herein means an HLA-A24 restrictive peptide derived from a cancer gene product HER2/neu, having a sequence of Thr Tyr Leu Pro Thr Asn Ala Ser Leu (SEQ ID NO: 3).

The term "MAGE3_A24 peptide" used herein means an HLA-A24 restrictive peptide derived from a cancer gene product MAGE3, having a sequence of Ile Met Pro Lys Ala Gly Leu Leu Ile (SEQ ID NO: 4).

The term "IPEP87 peptide" used herein means a peptide derived from hepatitis C virus (HCV) protein, having a sequence of Asp Leu Met Gly Tyr Ile Pro Ala Val (SEQ ID NO: 5).

The term "PR1 peptide" used herein means a peptide derived from a cancer gene product proteinase-3, having a sequence of Val Leu Gln Glu Leu Asn Val Thr Val (SEQ ID NO: 6).

The term "HER2/neu_A02 peptide" used herein means an HLA-A02 restrictive peptide derived from a cancer gene product HER2/neu, having a sequence of Lys Val Phe Gly Ser Leu Ala Phe Val (SEQ ID NO: 7).

The term "MAGE3_A02 peptide" used herein means an HLA-A02 restrictive peptide derived from a cancer gene product MAGE3, having a sequence of Lys Val Ala Glu Ile Val His Phe Leu (SEQ ID NO: 8).

The term "HBVenv peptide" used herein means a peptide derived from hepatitis B virus (HBV) protein, having a sequence of Trp Leu Ser Leu Leu Val Pro Phe Val (SEQ ID NO: 9).

The term "HER2/neu E75 peptide" used herein means a peptide derived from a product of cancer gene HER2/neu (HER2 protein), having a sequence of Lys Ile Phe Gly Ser Leu Ala Phe Leu (SEQ ID NO: 10).

The term "MUC1 peptide" used herein means a peptide derived from MUC1 protein which is a glycoprotein highly expressed on many cancer cells, having a sequence Ser Thr Ala Pro Pro Val His Asn Val (SEQ ID NO: 11).

In the injectable vaccine composition of the present invention, the antigen is required to be contained in an effective amount. For example, the antigen is preferably contained in an amount in the range of 0.01 to 10000 µg per a single dose in the injectable vaccine composition of the present invention. If the amount is less than 0.01 µg, the function as a prophylactic or therapeutic agent for cancers or infectious diseases can be insufficient, and if it is more than 10000 µg, the problem regarding the safety can arise. A more preferred lower limit of the antigen content is 0.1 µg, and a more preferred upper limit thereof is 5000 µg.

The injectable vaccine composition of the present invention contains an adjuvant.

As the adjuvant, a toll-like receptor 4 (TLR4) agonist can be recited. In the present invention, as the toll-like receptor 4 (TLR4) agonist, a specific lipopolysaccharide, or a derivative or a salt thereof is used.

The term "lipopolysaccharide" used herein refers to a lipopolysaccharide itself, or may be a derivative of a lipopolysaccharide as far as it has the property of the lipopolysaccharide. The salt used herein may be a salt of any organic acid or inorganic acid, and is preferably a pharmaceutically acceptable salt.

Here, a lipopolysaccharide (hereinafter, also referred to as an LPS) will be described.

An LPS is a composite compound composed of a lipid and a saccharide existing in the outer membrane surrounding peptide glycan of cell walls of gram-negative bacteria such as *Escherichia coli*, *Salmonella typhimurium*, and *Bordetella pertussis*, and is known as an active component of O antigen and endotoxin [J. M. Ghuysen and R. Hakenbeck ed., "New Comprehensive Biochemistry", Vol. 27, Bacterial Cell Wall, p. 18, Elsevier, 1994].

The basic structure of an LPS consists of three components: lipid A having a specific lipid, an oligosaccharide covalently bonded thereto, which is called an R core, and an O-specific polysaccharide ("Nikkei Biotechnology Up-to-date Glossary", p. 431, Nikkei Macgraw-hill, 1985).

The structure of the O-specific polysaccharide is the most diverse in the components, specific for the bacterial species, and shows the activity as a so-called O antigen. Generally, it is characterized by a structure in which oligosaccharides made up of several kinds of monosaccharides are repeated, however, the one composed of identical monosaccharides, or the one not having a repetitive structure is also known.

The injectable vaccine composition of the present invention contains a lipopolysaccharide derived from a specific gram-negative bacterium or a salt thereof, as an adjuvant. These are contained in many foods and herbal medicines, and hence assured to be safe to the living body, and extracts derived from these bacteria or modified substances thereof can also be used as they are.

Examples of bacteria from which a lipopolysaccharide for use in the adjuvant is derived include *Serratia* (species closely related to *Pantoea*/bread, meat, milk, one species of indigenous bacteria), *Leclercia* (species closely related to *Pantoea*/foods in general (soil bacteria)), *Rahnella* (species closely related to *Pantoea*/one species of indigenous bacteria), *Acidicaldus* (acetic bacteria/fermented food production), *Acidiphilium* (acetic bacteria/fermented food production), *Acidisphaera* (acetic bacteria/fermented food production), *Acidocella* (acetic bacteria/fermented food production), *Acidomonas* (acetic bacteria/fermented food production), *Asaia* (acetic bacteria/fermented food production), *Belnapia* (acetic bacteria/fermented food production), *Craurococcus* (acetic bacteria/fermented food production), *Gluconacetobacter* (acetic bacteria/fermented food production), *Gluconobacter* (acetic bacteria/fermented food production), *Kozakia* (acetic bacteria/fermented food production), *Leahibacter* (acetic bacteria/fermented food production), *Muricoccus* (acetic bacteria/fermented food production), *Neoasaia* (acetic bacteria/fermented food production), *Oleomonas* (acetic bacteria/fermented food production), *Paracraurococcus* (acetic bacteria/fermented food production), *Rhodopila* (acetic bacteria/fermented food production), *Roseococcus* (acetic bacteria/fermented food production), *Rubritepida* (acetic bacteria/fermented food production), *Saccharibacter* (acetic bacteria/fermented food production), *Stella* (acetic bacteria/fermented food production), *Swaminathania* (acetic bacteria/fermented food production), *Teichococcus* (acetic bacteria/fermented food production), *Zavarzinia* (acetic bacteria/fermented food production), *Pseudomonas* (*Pseudomonas* bacteria/beef, egg, meat, fish, vegetable), *Achromobacter* (*Achromobacter* bacteria/fish, meat), *Bacillus* (*Bacillus* bacteria/rice, vegetable), *Methanoculleus* (methane-producing bacteria/methane-producing bacterium parasitizing on animal intestines), *Methanosarcina* (methane-producing bacteria/methane-producing bacterium parasitizing on animal intestines), *Clostridium* (*Clostridium* bacteria/meat, milk, vegetable, canned food), *Micrococcus* (*Actinomycetes*/meat, fish), *Flavobacterium* (*Bacteroides* bacteria/putrefactive bacterium of food), *Pantoea, Acetobacter, Zymomonas, Xanthomonas*, and *Enterobacter*. These are assured to be safe to the living body because these are contained in many foods, or used in the course of producing foods.

Among these, at least one selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pantoea, Acetobacter, Zymomonas, Xanthomonas*, and *Enterobacter* is preferred.

More preferably, the gram-negative bacterium is at least one selected from the group consisting of *Pantoea, Acetobacter, Zymomonas, Xanthomonas*, and *Enterobacter*. In particular, a lipopolysaccharide derived from *Pantoea* is currently used as a health food, and is particularly effective when it is orally administered. Extracts derived from these bacteria or modified substances thereof can also be used as they are.

When a lipopolysaccharide derived from the gram-negative bacterium or a salt thereof is used, it is generally necessary to take the safety of the living body into account, and a modified substance may be used to detoxify the same.

As the toll-like receptor 4 (TLR4) agonist, a derivative of the aforementioned specific lipopolysaccharide, for example, lipid A from which a polysaccharide moiety is removed or monophosphoryl lipid A, 3-deacylated MPL and so on are recited, or the agonist may be a salt.

The lipid A from which a polysaccharide moiety of a lipopolysaccharide is removed can be an isolate derived from the specific gram-negative bacterium, or can be a synthetic product having the same structure as the isolate derived from the gram-negative bacterium.

As the modified substance of the lipid A, dephosphorylated monophosphoryl lipid (MPL) or a salt thereof is preferably used. The monophosphoryl lipid used herein may be monophosphoryl lipid itself, and a derivative thereof as far as the property is possessed. In particular, 3-deacylated monophosphoryl lipid (3D-MPL) that has already been proven as an adjuvant in medical use, or synthetic glucopyranosyl lipid that is not deacylated, proposed in US Patent Application No. 2010/0310602 is preferred from the view point of safety in a living body.

Also as the monophosphoryl lipid, the one derived from *Salmonella typhimurium* having safety and precedent use is preferably used.

In the present invention, an LPS derived from *Pantoea agglomerans* is further preferably used. Among others, the LPS derived from *Pantoea agglomerans* is preferably an LPS derived from *Pantoea agglomerans* having a molecular weight determined by the SDS-PAGE method using protein markers of 5000±3000, preferably 5000±2000. The molecular weight used herein is measured by the position of the stained band by the SDS-PAGE method using protein markers, and the details will be described later.

The LPS derived from *Pantoea agglomerans* that is also preferably used in the present invention is a lipopolysaccharide wherein the O-antigen moiety is formed of a repeating structure of rhamnose and glucose.

The LPS derived from *Pantoea agglomerans* can be produced by culturing *Pantoea agglomerans* by an ordinary method, collecting the bacterial cells from the culture medium, and purifying the collected bacterial cells according to a known method.

The molecular weight of the LPS derived from *Pantoea agglomerans* can be measured in the following manner.

That is, for an LPS derived from *Pantoea agglomerans* prepared as a blend, or for an LPS derived from *Pantoea agglomerans* extracted and purified from a vaccine composition by an appropriate method, the molecular weight can be determined in the following manner.

An LPS derived from *Pantoea agglomerans* is dissolved in distilled water to prepare a 1 mg/mL solution, equivalent amounts of the solution and Sample buffer solution 2ME+ (available from WAKO) are mixed, and the mixture is dipped in a boiling water bath for 5 minutes, and then immediately dipped in ice water and rapidly cooled.

A slab gel electrophoresis tank (available from Marisol) is filled with a running buffer (available from ATTO), 20% polyacrylamide gel is fixed in the electrophoresis tank, each 10 μL of sample is put into a sample groove, and running is continued for at least one hour at a voltage of 100 V until the pigment is eluted from the gel. After end of the running, silver staining is conducted with a silver staining kit 161-0443 (available from Bio-Rad) at room temperature, and the behavior is checked.

In the injectable vaccine composition of the present invention, the ratio of the mass of the adjuvant relative to the mass of the vaccine antigen (total mass of the adjuvant/total mass of the antigen) is preferably in the range of 0.002 to 50, for example. If the ratio is less than 0.002, the function as a prophylactic or therapeutic agent for cancers or infectious diseases can be insufficient, whereas if it is more than 50, the problem regarding the safety can arise. A more preferred lower limit of the ratio is 0.01, and a more preferred upper limit thereof is 10.

Also, in the injectable vaccine composition of the present invention, as the adjuvant, those described above and a different conventionally known adjuvant may be used in combination as long as a specific lipopolysaccharide derived from a gram-negative bacterium or a salt thereof is contained.

The injectable vaccine composition of the present invention can be prepared by adding other ingredients (e.g., phosphate buffer solution) as needed to the aforementioned antigen and adjuvant, and stirring and mixing them by a known method, and further heating, cooling, or drying without heating as needed by a known method.

Also, by using the injectable vaccine composition of the present invention, it is possible to prepare a liquid preparation, an emulsion preparation, or a semi-solid preparation or a solid preparation that is dissolved, emulsified or suspended before use by addition of a liquid. Besides these materials, an antiseptic, an antioxidant, a stabilizer, a surfactant and the like may be appropriately used as desired.

These materials are not particularly limited, and those conventionally known can be used.

The injectable vaccine composition of the present invention is particularly preferably a liquid preparation, an emulsion preparation, or a semi-solid preparation or a solid preparation that is dissolved or suspended before use by addition of a liquid. As will be described later, when the injectable vaccine composition of the present invention is a liquid preparation, an emulsion preparation, or the solid preparation that is dissolved, emulsified or suspended before use by addition of a liquid, it can be more favorably administered to a human being or an animal by injection.

The injectable vaccine composition of the present invention is administered to a human being or an animal (mammal, Aves, etc.) by injection.

The administration method of the injectable vaccine composition of the present invention is not particularly limited, and it is preferably administered by any one of intracutaneous injection, subcutaneous injection, and intramuscular injection.

Advantageous Effects of Invention

Since the injectable vaccine composition of the present invention contains the aforementioned specific adjuvant together with at least one antigen, it can effectively induce the systemic immune response, for example, the humoral immunity or cellular immunity by being administered by injection.

DESCRIPTION OF EMBODIMENTS

Figure 1:
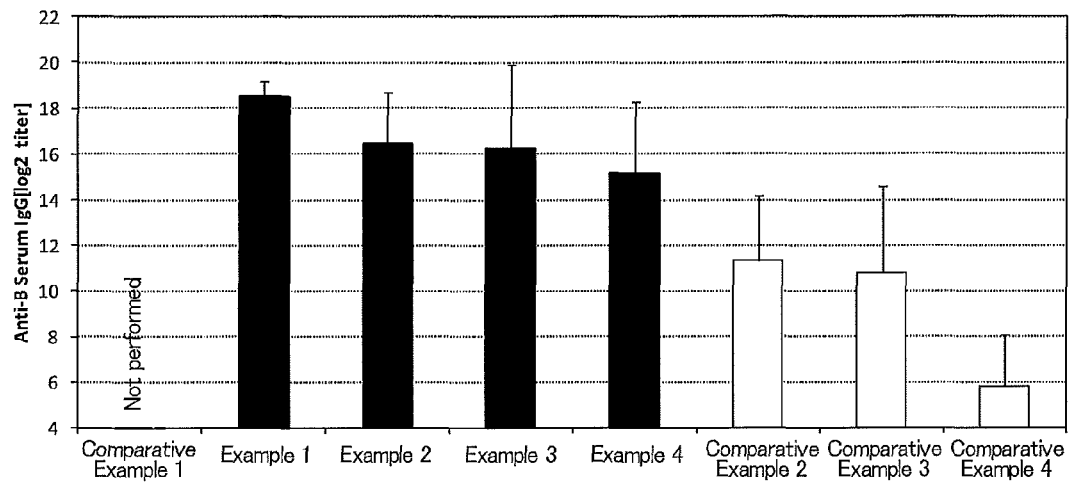
FIG. 1 is a graph showing results of influenza HA (type B)-specific IgG titers in a mouse serum in Examples 1 to 4 and Comparative Examples 1 to 4.

The present invention will be described in more detail with reference to the following examples, but is not limited to these examples.

Examples 1 to 4, Comparative Examples 1 to 4

For each of the following administration groups, a vaccine composition was prepared for ten animals.

the prepared vaccine composition was subcutaneously administered to each mouse. After one week from the second administration, a mouse serum was collected, and an influenza HA (type B)-specific IgG titer in the serum was determined by the ELISA method. Specific determination methods will be described later.

In the group in which 100 μg of the adjuvant was administered (Comparative Example 1), impairment in the lie of hair, and weight loss of mice were observed after 24 hours from the first administration, and the mice were euthanized. Therefore, the subsequent measurement of the antibody titer was not conducted. An adjuvant is a substance that activates immunity, and it is apparent that the immunity can be obtained more easily as the amount added increases. However, administering an excessive amount is problematic in terms of safety, and administration of 100 μg in mice was not conducted after Comparative Example 1.

Specific determination methods will be described later.

TABLE 1

| No. | Vaccine antigen Species | Amount [μg/mouse/dose] | Adjuvant (LPS derived from *Pantoea agglomerans*) Amount [μg/mouse/dose] | Ratio (adjuvant/antigen) | Administration route |
|---|---|---|---|---|---|
| Comparative Example 1 | B/Wisconsin/1/2010 | 1 | 100 | 100 | Subcutaneous |
| Example 1 | B/Wisconsin/1/2010 | 1 | 10 | 10 | Subcutaneous |
| Example 2 | B/Wisconsin/1/2010 | 1 | 1 | 1 | Subcutaneous |
| Example 3 | B/Wisconsin/1/2010 | 1 | 0.1 | 0.1 | Subcutaneous |
| Example 4 | B/Wisconsin/1/2010 | 1 | 0.01 | 0.01 | Subcutaneous |
| Comparative Example 2 | B/Wisconsin/1/2010 | 1 | 0.001 | 0.001 | Subcutaneous |
| Comparative Example 3 | B/Wisconsin/1/2010 | 1 | 0 | 0 | Subcutaneous |
| Comparative Example 4 | — | — | — | — | Subcutaneous |

An influenza vaccine antigen-containing solution (B/Wisconsin/1/2010, produced by The Research Foundation for Microbial Diseases of Osaka University) (445 μg/mL), and a solution of a lipopolysaccharide derived from *Pantoea agglomerans* (available from Institute of applied technology for innate immunity) (5 mg/mL) were prepared to give doses in each group of Table 1, and then a phosphate buffer (available from Nacalai Tesque) was added to prepare 1000 μL of a vaccine composition. For example, in Example 1, after adding 22.5 μL of the influenza vaccine antigen-containing solution, and 20 μL of a solution of the lipopolysaccharide derived from *Pantoea agglomerans*, a phosphate buffer was added to make the total amount 1000 μL. For other examples and comparative examples, vaccine compositions were prepared to have the contents corresponding to the doses by appropriate dilution, and in Comparative Example 4, only a phosphate buffer (available from Nacalai Tesque) was administered to mice without adding a vaccine antigen or an adjuvant.

Six mice (female BALB/C mice aged 8 weeks, Japan SLC, Inc.) were anesthetized, and 100 μL of the prepared vaccine composition was subcutaneously administered to each mouse by injection. After one week from the administration, the mice were anesthetized again, and 100 μL of Examples 5 to 8, Comparative Examples 5 to 7

Vaccine compositions corresponding to Table 2 were prepared in the procedure based on that in Examples 1 to 4 and Comparative Examples 1 to 4 except that the influenza vaccine antigen-containing solution was changed from B/Wisconsin/1/2010 to A/California/07/2009 (H1N1, produced by The Research Foundation for Microbial Diseases of Osaka University) (801 μg/mL). For example, in Example 5, after adding 12.5 μL of an influenza vaccine antigen-containing solution and 20 μL of a solution of a lipopolysaccharide derived from *Pantoea agglomerans*, a phosphate buffer was added to make the total amount 1000 μL.

Six mice (female BALB/C mice aged 8 weeks, Japan SLC, Inc.) were anesthetized, and 100 μL of the prepared vaccine composition was subcutaneously administered to each mouse. After one week from the administration, the mice were anesthetized again, and 100 μL of the prepared vaccine composition was subcutaneously administered to each mouse. After one week from the second administration, a mouse serum was collected, and an influenza HA (H1N1)-specific IgG titer in the serum was determined by the ELISA method. Specific determination methods will be described later.

TABLE 2

| No. | Vaccine antigen | | Adjuvant (LPS derived from *Pantoea agglomerans*) | | Administration route |
| | Species | Amount [μg/mouse/dose] | Amount [μg/mouse/dose] | Ratio (adjuvant/antigen) | |
| --- | --- | --- | --- | --- | --- |
| Example 5 | A/California/07/2009(H1N1) | 1 | 10 | 10 | Subcutaneous |
| Example 6 | A/California/07/2009(H1N1) | 1 | 1 | 1 | Subcutaneous |
| Example 7 | A/California/07/2009(H1N1) | 1 | 0.1 | 0.1 | Subcutaneous |
| Example 8 | A/California/07/2009(H1N1) | 1 | 0.01 | 0.01 | Subcutaneous |
| Comparative Example 5 | A/California/07/2009(H1N1) | 1 | 0.001 | 0.001 | Subcutaneous |
| Comparative Example 6 | A/California/07/2009(H1N1) | 1 | 0 | 0 | Subcutaneous |
| Comparative Example 7 | — | — | — | — | Subcutaneous |

Example 9, Comparative Examples 8 to 10

Using a pneumococcal capsular polysaccharide-containing solution (Pneumovax NP, available from MSD K.K.) (1150 μg/mL), and a solution of a lipopolysaccharide derived from *Pantoea agglomerans* (available from Institute of applied technology for innate immunity) (5 mg/mL) in Example 9, or glucopyranosyl lipid (MPLAs, available from InvivoGen) in Comparative Example 8, a composition was prepared to satisfy the dose of each group in Table 3, and a phosphate buffer (available from Nacalai Tesque) was added to give 1000 μL of a vaccine composition. For example, in Example 9, after adding 8.7 μL of a pneumococcal capsular polysaccharide-containing solution and 2 μL of a solution of a lipopolysaccharide derived from *Pantoea agglomerans*, a phosphate buffer was added to make the total amount 1000 μL. In Comparative Example 9, only the pneumococcal capsular polysaccharide-containing solution was administered to mice, and in Comparative Example 10, only the phosphate buffer (available from Nacalai Tesque) was administered to mice.

Six mice (female BALB/C mice aged 8 weeks, Japan SLC, Inc.) were anesthetized, and 100 μL of the prepared vaccine composition was subcutaneously administered to each mouse. After one week from the administration, the mice were anesthetized again, and 100 μL of the prepared vaccine composition was subcutaneously administered to each mouse. After one week from the second administration, a mouse serum was collected, and a pneumococcal-specific IgG titer in the serum was determined by the ELISA method. Specific determination methods will be described later.

Example 10, Comparative Examples 11 to 13

Using an HPV16 recombinant protein-containing solution (HPV16, available from PROSPEC) (820 μg/mL), and a solution of a lipopolysaccharide derived from *Pantoea agglomerans* (available from Institute of applied technology for innate immunity) (5 mg/mL) in Example 10, or glucopyranosyl lipid (MPLAs, available from InvivoGen) in Comparative Example 11, a composition was prepared to satisfy the dose of each group in Table 4, and a phosphate buffer (available from Nacalai Tesque) was added to give 1000 μL of a vaccine composition. For example, in Example 10, after adding 12.2 μL of an HPV16 recombinant protein-containing solution and 2 μL of a solution of a lipopolysaccharide derived from *Pantoea agglomerans*, a phosphate buffer was added to make the total amount 1000 μL. In Comparative Example 12, only the HPV16 recombinant protein-containing solution was administered to mice, and in Comparative Example 13, only the phosphate buffer (available from Nacalai Tesque) was administered to mice.

Six mice (female BALB/C mice aged 8 weeks, Japan SLC, Inc.) were anesthetized, and 100 μL of the prepared vaccine composition was subcutaneously administered to each mouse. After one week from the administration, the mice were anesthetized again, and 100 μL of the prepared vaccine composition was subcutaneously administered to each mouse. After one week from the second administration, a mouse serum was collected, and an HPV16 recombinant protein-specific IgG titer in the serum was determined by the ELISA method. Specific determination methods will be described later.

TABLE 3

| No. | Vaccine antigen | | Adjuvant | | Administration route |
| | Species | Amount [μg/mouse/dose] | Amount [mouse/dose] | Note | |
| --- | --- | --- | --- | --- | --- |
| Example 9 | Pneumococcal capsular polysaccharide Pneumovax NP | 1 | LPS derived from *Pantoea agglomerans* 1[μg] | TLR4 ligand | Subcutaneous |
| Comparative Example 8 | Pneumococcal capsular polysaccharide Pneumovax NP | 1 | Glucopyranosyl lipid 1[μg] | TLR4 ligand | Subcutaneous |
| Comparative Example 9 | Pneumococcal capsular polysaccharide Pneumovax NP | 1 | — | — | Subcutaneous |
| Comparative Example 10 | — | — | — | — | Subcutaneous |

TABLE 4

| No. | Vaccine antigen Species | Amount [μg/mouse/dose] | Adjuvant Amount [μg/mouse/dose] | Note | Administration route |
|---|---|---|---|---|---|
| Example 10 | HPV16 recombinant protein | 1 | LPS derived from *Pantoea agglomerans* 1[μg] | TLR4 ligand | Subcutaneous |
| Comparative Example 11 | HPV16 recombinant protein | 1 | Glucopyranosyl lipid 1[μg] | TLR4 ligand | Subcutaneous |
| Comparative Example 12 | HPV16 recombinant protein | 1 | — | — | Subcutaneous |
| Comparative Example 13 | — | — | — | — | Subcutaneous |

Examples 11 to 13, Comparative Example 14

To 200 μL of an attenuated live rotavirus-containing solution (RotaTeq mixture for internal use, available from MSD K.K.), 50 μL (2 mg/mL) in Example 11, 5 μL in Example 12, or 0.5 μL in Example 13 of a solution of a lipopolysaccharide derived from *Pantoea agglomerans* (available from Nacalai Tesque), or 5 μL of a solution of a glucopyranosyl lipid (MPLAs, available from InvivoGen) (2 mg/mL) in Comparative Example 14 was added, and a phosphate buffer (available from Nacalai Tesque) was added to prepare 1000 μL of a vaccine composition.

Six mice (female BALB/C mice aged 8 weeks, Japan SLC, Inc.) are anesthetized, and 100 μL of the prepared vaccine composition is subcutaneously administered to each mouse. After one week from the administration, the mice are anesthetized again, and 100 μL of the prepared vaccine composition is subcutaneously administered to each mouse. After one week from the second administration, a mouse serum is collected, and an antigen-specific IgG titer in the serum is determined by the ELISA method.

Examples 14 to 52, Comparative Examples 15 to 27

A vaccine composition was prepared in the same manner as in Examples 11 to 13, and Comparative Example 14 except that in Examples 14 to 16, and Comparative Example 15, an inactivated poliovirus-containing solution (IMOVAX POLIO subcutaneous, available from Sanofi K.K.) was used, in Examples 17 to 19, and Comparative Example 16, an inactivated hepatitis A virus-containing solution (Aimmugen, available from KAKETSUKEN) was used, in Examples 20 to 22, and Comparative Example 17, an inactivated Japanese encephalitis virus-containing solution (ENCEVAC for subcutaneous injection, available from KAKETSUKEN) was used, in Examples 23 to 25, and Comparative Example 18, an attenuated live mumps virus-containing solution (mumps live vaccine, available from KITASATO DAIICHISANKYO VACCINE CO., LTD.) was used, in Examples 26 to 28, and Comparative Example 19, an attenuated live measles virus-containing solution (measles live vaccine, available from KITASATO DAIICHISANKYO VACCINE CO., LTD.) was used, in Examples 29 to 31, and Comparative Example 20, an attenuated live rubella virus-containing solution (dry attenuated live rubella vaccine, available from KITASATO DAIICHISANKYO VACCINE CO., LTD.) was used, in Examples 32 to 34, and Comparative Example 21, a tetanus toxoid conjugate *Haemophilus* influenzae type b polysaccharide-containing solution (ActHIB, available from Sanofi K. K.) was used, in Examples 35 to 37, and Comparative Example 22, a recombinant HBs antigen protein-containing solution (Bimmugen, available from KAKETSUKEN) was used, in Examples 38 to 40, and Comparative Example 23, an attenuated live yellow fever virus-containing solution (yellow fever vaccine, available from Sanofi K.K.) was used, in Examples 41 to 43, and Comparative Example 24, a tetanus toxoid-containing solution (tetanus toxoid, available from DENKA SEIKEN CO., LTD.) was used, in Examples 44 to 46, and Comparative Example 25, an attenuated live chickenpox virus-containing solution (dry attenuated live chickenpox vaccine, available from The Research Foundation for Microbial Diseases of Osaka University) was used, in Examples 47 to 49, and Comparative Example 26, a live BCG-containing solution (dry BCG vaccine, available from Japan BCG Laboratory) was used, and in Examples 50 to 52, and Comparative Example 27, an inactivated rabies virus-containing solution (tissue-cultured inactivated rabies vaccine, available from KAKETSUKEN) was used so that the dose of each group in Table 5 was satisfied. Also immunological experiments are conducted in the same manner as in Examples 11 to 13, and Comparative Example 14.

TABLE 5

| | Vaccine antigen | | | Adjuvant | | | |
|---|---|---|---|---|---|---|---|
| No. | Speecies | Amount [/mouse/dose] | Substance name | Ligand | Amount [μg/mouse/dose] | Administration route | Note |
| Example 11 | Live attenuated *rotavirus* (RIX4414 strain) | Vaccine 20 μL equivalent | LPS derived from *Pantoea agglomerans* | TLR4 | 10 | Subcutaneous | Liquid |
| Example 12 | Live attenuated *rotavirus* (RIX4414 strain) | Vaccine 20 μL equivalent | LPS derived from *Pantoea agglomerans* | TLR4 | 1 | Subcutaneous | Liquid |
| Example 13 | Live attenuated *rotavirus* (RIX4414 strain) | Vaccine 20 μL equivalent | LPS derived from *Pantoea agglomerans* | TLR4 | 0.1 | Subcutaneous | Liquid |
| Example 14 | Inactivated *poliovirus* (type 1, type 2, type 3) | Vaccine 20 μL equivalent | LPS derived from *Pantoea agglomerans* | TLR4 | 10 | Subcutaneous | Liquid |

TABLE 5-continued

| No. | Vaccine antigen Speecies | Amount [/mouse/dose] | Adjuvant Substance name | Ligand | Amount [μg/mouse/dose] | Administration route | Note |
|---|---|---|---|---|---|---|---|
| Example 15 | Inactivated *poliovirus* (type 1, type 2, type 3) | Vaccine 20 μL equivalent | LPS derived from *Pantoea agglomerans* | TLR4 | 1 | Subcutaneous | Liquid |
| Example 16 | Inactivated *poliovirus* (type 1, type 2, type 3) | Vaccine 20 μL equivalent | LPS derived from *Pantoea agglomerans* | TLR4 | 0.1 | Subcutaneous | Liquid |
| Example 17 | Inactivated hepatitis A virus | Vaccine 200 μL equivalent | LPS derived from *Pantoea agglomerans* | TLR4 | 10 | Subcutaneous | Liquid |
| Example 18 | Inactivated hepatitis A virus | Vaccine 200 μL equivalent | LPS derived from *Pantoea agglomerans* | TLR4 | 1 | Subcutaneous | Liquid |
| Example 19 | Inactivated hepatitis A virus | Vaccine 200 μL equivalent | LPS derived from *Pantoea agglomerans* | TLR4 | 0.1 | Subcutaneous | Liquid |
| Example 20 | Inactivated Japanese encephalitis virus | Vaccine 20 μL equivalent | LPS derived from *Pantoea agglomerans* | TLR4 | 10 | Subcutaneous | Liquid |
| Example 21 | Inactivated Japanese encephalitis virus | Vaccine 20 μL equivalent | LPS derived from *Pantoea agglomerans* | TLR4 | 1 | Subcutaneous | Liquid |
| Example 22 | Inactivated Japanese encephalitis virus | Vaccine 20 μL equivalent | LPS derived from *Pantoea agglomerans* | TLR4 | 0.1 | Subcutaneous | Liquid |
| Example 23 | Live attenuated *mumps virus* | Vaccine 20 μL equivalent | LPS derived from *Pantoea agglomerans* | TLR4 | 10 | Subcutaneous | Liquid |
| Example 24 | Live attenuated *mumps virus* | Vaccine 20 μL equivalent | LPS derived from *Pantoea agglomerans* | TLR4 | 1 | Subcutaneous | Liquid |
| Example 25 | Live attenuated *mumps virus* | Vaccine 20 μL equivalent | LPS derived from *Pantoea agglomerans* | TLR4 | 0.1 | Subcutaneous | Liquid |
| Example 26 | Live attenuated *measles virus* | Vaccine 20 μL equivalent | LPS derived from *Pantoea agglomerans* | TLR4 | 10 | Subcutaneous | Liquid |
| Example 27 | Live attenuated *measles virus* | Vaccine 20 μL equivalent | LPS derived from *Pantoea agglomerans* | TLR4 | 1 | Subcutaneous | Liquid |
| Example 28 | Live attenuated *measles virus* | Vaccine 20 μL equivalent | LPS derived from *Pantoea agglomerans* | TLR4 | 0.1 | Subcutaneous | Liquid |
| Example 29 | Live attenuated *rubella virus* | Vaccine 20 μL equivalent | LPS derived from *Pantoea agglomerans* | TLR4 | 10 | Subcutaneous | Liquid |
| Example 30 | Live attenuated *rubella virus* | Vaccine 20 μL equivalent | LPS derived from *Pantoea agglomerans* | TLR4 | 1 | Subcutaneous | Liquid |
| Example 31 | Live attenuated *rubella virus* | Vaccine 20 μL equivalent | LPS derived from *Pantoea agglomerans* | TLR4 | 0.1 | Subcutaneous | Liquid |
| Example 32 | Tetanus toxoid-conjugated *Haemophilus influenzae* type b polysaccharide | Vaccine 20 μL equivalent | LPS derived from *Pantoea agglomerans* | TLR4 | 10 | Subcutaneous | Liquid |
| Example 33 | Tetanus toxoid-cojugated *Haemophilus influenzae* type b polysaccharide | Vaccine 20 μL equivalent | LPS derived from *Pantoea agglomerans* | TLR4 | 1 | Subcutaneous | Liquid |
| Example 34 | Tetanus toxoid-co jugated *Haemophilus influenzae* type b polysaccharide | Vaccine 20 μL equivalent | LPS derived from *Pantoea agglomerans* | TLR4 | 0.1 | Subcutaneous | Liquid |
| Example 35 | Recombinant HBs antigen protein | Vaccine 20 μL equivalent | LPS derived from *Pantoea agglomerans* | TLR4 | 10 | Subcutaneous | Liquid |
| Example 36 | Recombinant HBs antigen protein | Vaccine 20 μL equivalent | LPS derived from *Pantoea agglomerans* | TLR4 | 1 | Subcutaneous | Liquid |
| Example 37 | Recombinant HBs antigen protein | Vaccine 20 μL equivalent | LPS derived from *Pantoea agglomerans* | TLR4 | 0.1 | Subcutaneous | Liquid |
| Example 38 | Live attenuated yellow fever virus | Vaccine 20 μL equivalent | LPS derived from *Pantoea agglomerans* | TLR4 | 10 | Subcutaneous | Liquid |
| Example 39 | Live attenuated yellow fever virus | Vaccine 20 μL equivalent | LPS derived from *Pantoea agglomerans* | TLR4 | 1 | Subcutaneous | Liquid |
| Example 40 | Live attenuated yellow fever virus | Vaccine 20 μL equivalent | LPS derived from *Pantoea agglomerans* | TLR4 | 0.1 | Subcutaneous | Liquid |
| Example 41 | Tetanus toxoid | Vaccine 20 μL equivalent | LPS derived from *Pantoea agglomerans* | TLR4 | 10 | Subcutaneous | Liquid |
| Example 42 | Tetanus toxoid | Vaccine 20 μL equivalent | LPS derived from *Pantoea agglomerans* | TLR4 | 1 | Subcutaneous | Liquid |
| Example 43 | Tetanus toxoid | Vaccine 20 μL equivalent | LPS derived from *Pantoea agglomerans* | TLR4 | 0.1 | Subcutaneous | Liquid |
| Example 44 | Live attenuated *varicella-zoster* virus | Vaccine 20 μL equivalent | LPS derived from *Pantoea agglomerans* | TLR4 | 10 | Subcutaneous | Liquid |
| Example 45 | Live attenuated *varicella-zoster* virus | Vaccine 20 μL equivalent | LPS derived from *Pantoea agglomerans* | TLR4 | 1 | Subcutaneous | Liquid |
| Example 46 | Live attenuated *varicella-zoster* virus | Vaccine 20 μL equivalent | LPS derived from *Pantoea agglomerans* | TLR4 | 0.1 | Subcutaneous | Liquid |
| Example 47 | Live BCG | Vaccine 0.02 μL equivalent | LPS derived from *Pantoea agglomerans* | TLR4 | 10 | Subcutaneous | Liquid |
| Example 48 | Live BCG | Vaccine 0.02 μL equivalent | LPS derived from *Pantoea agglomerans* | TLR4 | 1 | Subcutaneous | Liquid |
| Example 49 | Live BCG | Vaccine 0.02 μL equivalent | LPS derived from *Pantoea agglomerans* | TLR4 | 0.1 | Subcutaneous | Liquid |

TABLE 5-continued

| No. | Vaccine antigen Speecies | Amount [/mouse/dose] | Adjuvant Substance name | Ligand | Amount [µg/mouse/dose] | Administration route | Note |
|---|---|---|---|---|---|---|---|
| Example 50 | Inactivated *rabies virus* | Vaccine 20 µL equivalent | LPS derived from *Pantoea agglomerans* | TLR4 | 10 | Subcutaneous | Liquid |
| Example 51 | Inactivated *rabies virus* | Vaccine 20 µL equivalent | LPS derived from *Pantoea agglomerans* | TLR4 | 1 | Subcutaneous | Liquid |
| Example 52 | Inactivated *rabies virus* | Vaccine 20 µL equivalent | LPS derived from *Pantoea agglomerans* | TLR4 | 0.1 | Subcutaneous | Liquid |
| Comparative Example 14 | Live attenuated *rotavirus* (RIX4414 strain) | Vaccine 20 µL equivalent | Glucopyranosyl lipid | TLR4 | 1 | Subcutaneous | Liquid |
| Comparative Example 15 | Inactivated *poliovirus* (type 1, type 2, type 3) | Vaccine 20 µL equivalent | Glucopyranosyl lipid | TLR4 | 1 | Subcutaneous | Liquid |
| Comparative Example 16 | Inactivated hepatitis A virus | Vaccine 20 µL equivalent | Glucopyranosyl lipid | TLR4 | 1 | Subcutaneous | Liquid |
| Comparative Example 17 | Inactivated Japanese encephalitis virus | Vaccine 20 µL equivalent | Glucopyranosyl lipid | TLR4 | 1 | Subcutaneous | Liquid |
| Comparative Example 18 | Live attenuated *mumps virus* | Vaccine 20 µL equivalent | Glucopyranosyl lipid | TLR4 | 1 | Subcutaneous | Liquid |
| Comparative Example 19 | Live attenuated *measles virus* | Vaccine 20 µL equivalent | Glucopyranosyl lipid | TLR4 | 1 | Subcutaneous | Liquid |
| Comparative Example 20 | Live attenuated *rubella virus* | Vaccine 20 µL equivalent | Glucopyranosyl lipid | TLR4 | 1 | Subcutaneous | Liquid |
| Comparative Example 21 | Tetanus toxoid-conjugated *Haemophilus influenzae* type b polysaccharide | Vaccine 20 µL equivalent | Glucopyranosyl lipid | TLR4 | 1 | Subcutaneous | Liquid |
| Comparative Example 22 | Recombinant HBs antigen protein | Vaccine 20 µL equivalent | Glucopyranosyl lipid | TLR4 | 1 | Subcutaneous | Liquid |
| Comparative Example 23 | Live attenuated yellow fever virus | Vaccine 20 µL equivalent | Glucopyranosyl lipid | TLR4 | 1 | Subcutaneous | Liquid |
| Comparative Example 24 | Tetanus toxoid | Vaccine 20 µLequivalent | Glucopyranosyl lipid | TLR4 | 1 | Subcutaneous | Liquid |
| Comparative Example 25 | Live attenuated *varicella-zoster* virus | Vaccine 20 µL equivalent | Glucopyranosyl lipid | TLR4 | 1 | Subcutaneous | Liquid |
| Comparative Example 26 | Live BCG | Vaccine 20 µL equivalent | Glucopyranosyl lipid | TLR4 | 1 | Subcutaneous | Liquid |
| Comparative Example 27 | Inactivated *rabies virus* | Vaccine 20 µL equivalent | Glucopyranosyl lipid | TLR4 | 1 | Subcutaneous | Liquid |

(Mouse Immunological Experiments)

For female BALB/c mice aged 8 weeks, administration was conducted twice at an interval of one week. After one week from the last administration, blood and a nasal cavity washing liquid of each mouse were collected. The blood was centrifuged at 3000 G for 10 minutes at 4° C., and 300 µL of a phosphate buffer (available from Nacalai Tesque) was added to 20 µL of the supernatant to prepare a serum sample. By measuring an antigen-specific IgG titer in a mouse serum or the like, the systemic immune response was evaluated. The evaluation method will be described below.

Figure 2:
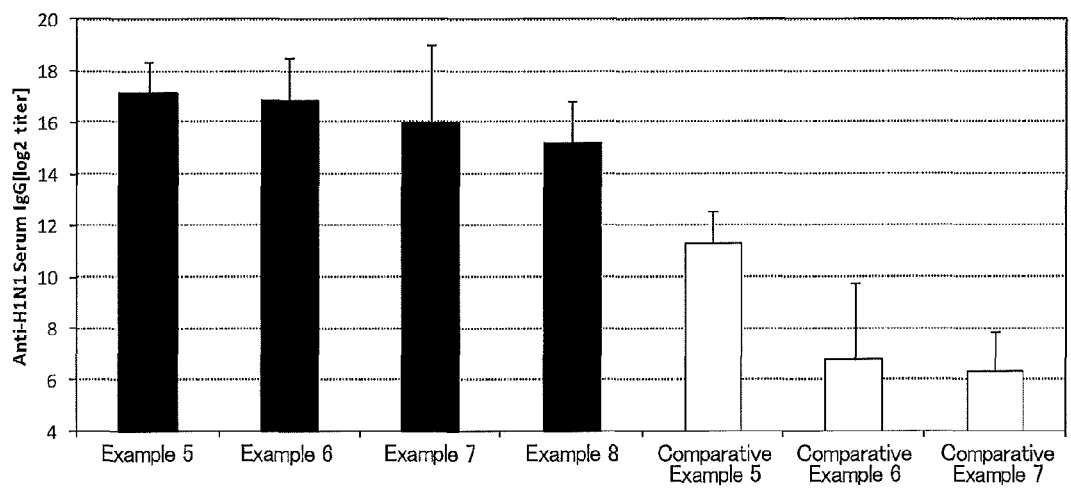
FIG. 2 is a graph showing results of influenza HA (H1N1)-specific IgG titers in a mouse serum in Examples 5 to 8 and Comparative Examples 5 to 7.
Figure 3:
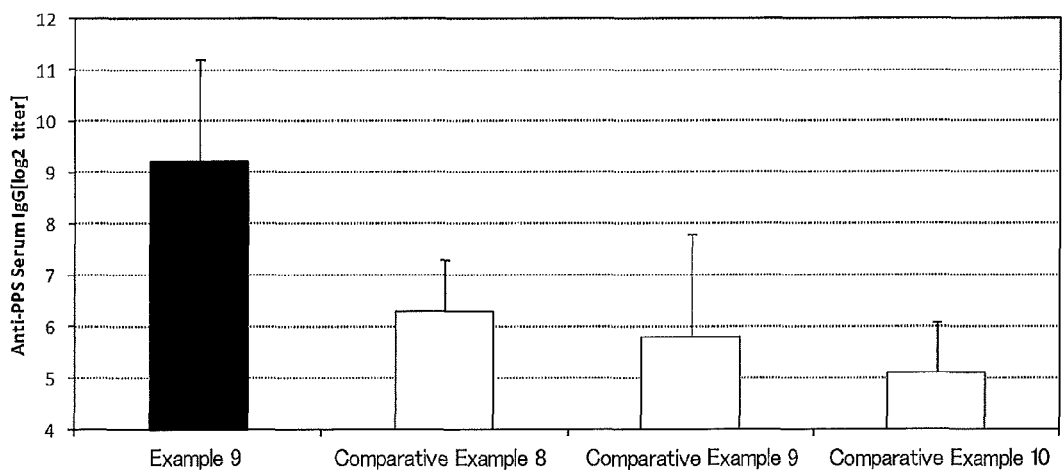
FIG. 3 is a graph showing results of pneumococcal-specific IgG titers in a mouse serum in Example 9 and Comparative Examples 8 to 10.
Figure 4:
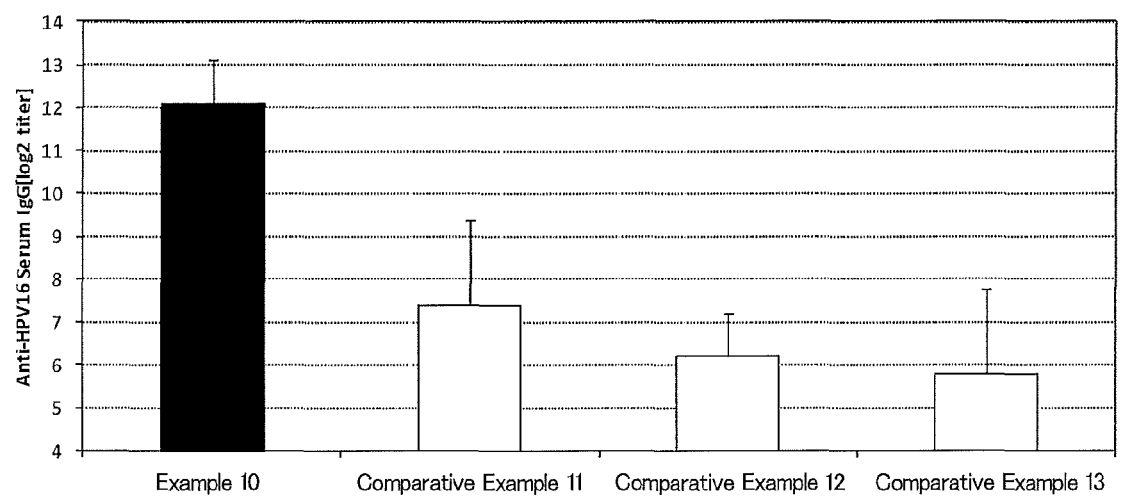
FIG. 4 is a graph showing results of HPV16 recombinant protein-specific IgG titers in a mouse serum in Example 10 and Comparative Examples 11 to 13.

The respective evaluation results are shown in FIGS. 1 to 4.

(Method for Measuring Antigen-Specific IgG Titer in Mouse Serum (ELISA Method))

In a 96-well plate for ELISA, each 100 µL of each antigen (for example, a pneumococcal capsular polysaccharide antigen solution in measurement of a pneumococcal capsular polysaccharide-specific IgG antibody titer) diluted with a carbonate buffer (2.5 µg/mL) was added, and the plate was left still overnight.

Wells were washed with a preliminarily prepared Tween 20-containing PBS (hereinafter, referred to as a washing liquid) three times, and after adding each 200 µL of a blocking solution prepared by diluting a blocking agent (Block Ace, available from DS Pharma Biomedical Co., Ltd.) in purified water into 4 g/400 mL, the plate was left still for 2 hours at room temperature. Then, wells were washed with the washing liquid three times.

Using a solution prepared by diluting a blocking agent (Block Ace, available from DS Pharma Biomedical Co., Ltd.) with a phosphate buffer (available from Nacalai Tesque) into 0.4 g/100 mL (hereinafter, referred to as a reagent diluent), the aforementioned serum sample was diluted 15 times by doubling serial dilution, each 50 µL of the solutions were added, and the plate was left still for 2 hours at room temperature.

Then, the wells were washed three times with a washing liquid, and each 100 µL of an HRP-labeled anti-mouse IgG antibody (Goat-anti-mouse IgG Fc HRP, available from BETHYL) diluted 10000 times with the reagent diluent was added, and the plate was left still for 1 hour at room temperature.

Then, the wells were washed three times with a washing liquid, and each 100 µL of a TMB solution (ELISA POD TMB kit, available from Nacalai Tesque) was added. Then, each 100 µL of a 1 M sulfuric acid solution was added, and absorbance at 450 nm of the 96-well plate was measured by a micro plate reader (168-11135CAM, available from Bio-Rad). Based on the absorbance in the serial dilution, the maximum dilution fold at which the absorbance was not less than 0.1 was determined as an IgG titer in a mouse serum, and the value was determined as a value of Log 2.

Example 53, Comparative Examples 28 to 29

An emulsion injection was compounded and prepared to have the dose shown in Table 6. That is, after weighing a required amount of HER2/neu_E75 peptide (chemical synthetic product), a required amount of a solution of a lipopolysaccharide derived from *Pantoea agglomerans* (available from Institute of applied technology for innate immunity) (2 mg/mL) was added, and further a physiological saline solution (Otsuka Pharmaceutical) and Montanide ISA51VG (FREUND CORPORATION) were added in a liquid amount ratio of 1:1. Then, these were mingled by a homogenizer to prepare an emulsion injection. For each administration group, 1000 μL of the injection was prepared for 10 animals.

For example, in Example 53, 1 mg of HER2/neu_E75 peptide was weighed, and 50 μL of a solution of a lipopolysaccharide derived from *Pantoea agglomerans* (2 mg/mL) was added, and then 475 μL of a physiological saline solution (Otsuka Pharmaceutical) and 475 μL of Montanide ISA51VG (FREUND CORPORATION) were added. Then, these were mingled by a homogenizer to prepare an emulsion injection. In Comparative Example 28, 1 mg of HER2/neu_E75 peptide was weighed, and 500 μL of a physiological saline solution (Otsuka Pharmaceutical) and 500 μL of Montanide ISA51VG (FREUND CORPORATION) were added. Then, these were mingled by a homogenizer to prepare an emulsion injection. In Comparative Example 29, 500 μL of a physiological saline solution (Otsuka Pharmaceutical) and 500 μL of Montanide ISA51VG (FREUND CORPORATION) were added. Then, these were mingled by a homogenizer to prepare an emulsion injection.

These administration samples were administered to mice (gene modified mice for which cellular immunity induction by HLA-A*0201 type MHC restrictive peptide can be evaluated). Six mice were anesthetized, and then 100 μL of the prepared emulsion injection was subcutaneously administered to each mouse by injection. The number of times of administration is one. Induction level of antigen-specific cellular immunity was evaluated by the ELISPOT method. The specific experimental operations are based on the operating procedure of ELISPOT kit (R&D Systems). More specifically, a spleen was extracted after a lapse of six days from the administration, and a suspension of spleen cells was prepared. To wells of an ELISPOT plate to which anti mouse IFN-γ antibody is immobilized, spleen cells ($3 \times 10^6$ cells/well) and an antigen peptide (100 μM) were introduced together with a culture solution, and co-cultured for 20 hours in the culture conditions of 37° C. and 5% $CO_2$. The number of spots of IFN-γ-producing cells was evaluated.

Examples 54 to 63, Comparative Examples 30 to 39

In Example 54 and Comparative Example 30, survivin 2B (mouse for evaluation of immunity: BALB/c mouse) was used. In Example 55 and Comparative Example 31, GPC3 (mouse for evaluation of immunity: BALB/c mouse) was used. In Example 56 and Comparative Example 32, HER2/neu_A24 (mouse for evaluation of immunity: BALB/c mouse) was used. In Example 57 and Comparative Example 33, MAGE3_A24 (mouse for evaluation of immunity: BALE/c mouse) was used. In Example 58 and Comparative Example 34, IPEP87 (mouse for evaluation of immunity: gene modified mouse for which cellular immunity induction by HLA-A*0201 type MHC restrictive peptide can be evaluated) was used. In Example 59 and Comparative Example 35, PR1 (mouse for evaluation of immunity: gene modified mouse for which cellular immunity induction by HLA-A*0201 type MHC restrictive peptide can be evaluated) was used. In Example 60 and Comparative Example 36, HER2/neu_A02 (mouse for evaluation of immunity: gene modified mouse for which cellular immunity induction by HLA-A*0201 type MHC restrictive peptide can be evaluated) was used. In Example 61 and Comparative Example 37, MAGE3_A02 (mouse for evaluation of immunity: gene modified mouse for which cellular immunity induction by HLA-A*0201 type MHC restrictive peptide can be evaluated) was used. In Example 62 and Comparative Example 38, HBVenv (mouse for evaluation of immunity: gene modified mouse for which cellular immunity induction by HLA-A*0201 type MHC restrictive peptide can be evaluated) was used. In Example 63 and Comparative Example 39, MUC1 (mouse for evaluation of immunity: gene modified mouse for which cellular immunity induction by HLA-A*0201 type MHC restrictive peptide can be evaluated) was used. Compounding and preparation were conducted to satisfy the dose in Table 7, and immunological experiments were conducted in the same experimental procedure as in Example 53 and Comparative Examples 28 and 29. That is, each emulsion injection was subcutaneously administered, and immunity was examined by the ELISPOT method after six days from the administration.

TABLE 6

| No. | Vaccine antigen | | Adjuvant | | | Administration route |
|---|---|---|---|---|---|---|
| | Species | Amount [μg/mouse/dose] | | Amount [μg/mouse/dose] | Note | |
| Example 53 | HER2/neu_E75 | 100 | LPS derived from *Pantoea agglomerans* | 10[μg] | TLR4 ligand | Subcutaneous |
| Comparative Example 28 | HER2/neu_E75 | 100 | — | | — | Subcutaneous |
| Comparative Example 29 | — | — | — | | — | Subcutaneous |

TABLE 7

| No. | Vaccine antigen Species | Amount [μg/mouse/dose] | Adjuvant Amount [μg/mouse/dose] | Note | Administration route |
|---|---|---|---|---|---|
| Example 54 | Survivin 2B | 100 | LPS derived from *Pantoea agglomerans* 10[μg] | TLR4 ligand | Subcutaneous |
| Example 55 | GPC3 | 100 | LPS derived from *Pantoea agglomerans* 10[μg] | TLR4 ligand | Subcutaneous |
| Example 56 | HER2/neu_A24 | 100 | LPS derived from *Pantoea agglomerans* 10[μg] | TLR4 ligand | Subcutaneous |
| Example 57 | MAGE3_A24 | 100 | LPS derived from *Pantoea agglomerans* 10[μg] | TLR4 ligand | Subcutaneous |
| Example 58 | IPEP87 | 100 | LPS derived from *Pantoea agglomerans* 10[μg] | TLR4 ligand | Subcutaneous |
| Example 59 | PR1 | 100 | LPS derived from *Pantoea agglomerans* 10[μg] | TLR4 ligand | Subcutaneous |
| Example 60 | HER2/neu_A02 | 100 | LPS derived from *Pantoea agglomerans* 10[μg] | TLR4 ligand | Subcutaneous |
| Example 61 | MAGE3_A02 | 100 | LPS derived from *Pantoea agglomerans* 10[μg] | TLR4 ligand | Subcutaneous |
| Example 62 | HBVenv | 100 | LPS derived from *Pantoea agglomerans* 10[μg] | TLR4 ligand | Subcutaneous |
| Example 63 | MUC1 | 100 | LPS derived from *Pantoea agglomerans* 10[μg] | TLR4 ligand | Subcutaneous |
| Comparative Example 30 | Survivin 2B | 100 | — | — | Subcutaneous |
| Comparative Example 31 | GPC3 | 100 | — | — | Subcutaneous |
| Comparative Example 32 | HER2/neu_A24 | 100 | — | — | Subcutaneous |
| Comparative Example 33 | MAGE3_A24 | 100 | — | — | Subcutaneous |
| Comparative Example 34 | IPEP87 | 100 | — | — | Subcutaneous |
| Comparative Example 35 | PR1 | 100 | — | — | Subcutaneous |
| Comparative Example 36 | HER2/neu_A02 | 100 | — | — | Subcutaneous |
| Comparative Example 37 | MAGE3_A02 | 100 | — | — | Subcutaneous |
| Comparative Example 38 | HBVenv | 100 | — | — | Subcutaneous |
| Comparative Example 39 | MUC1 | 100 | — | — | Subcutaneous |

Figure 5:
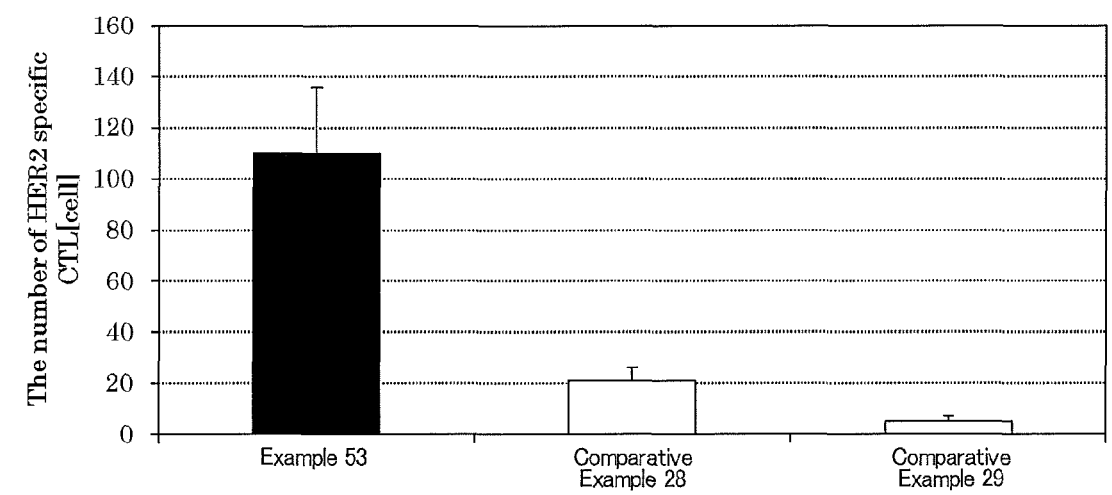
FIG. 5 is a graph showing results of the number of INFγ-producing cells in HER2/neu_E75-specific mouse spleen cells in Example 53 and Comparative Examples 28 to 29.
Figure 6:
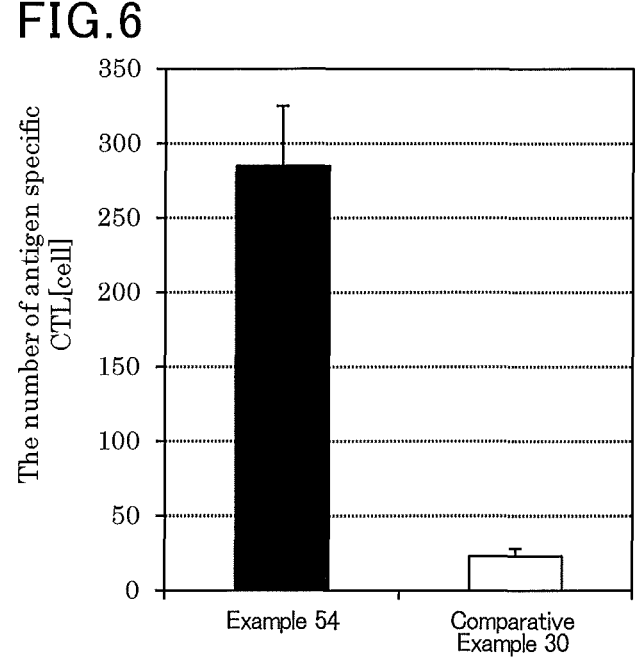
FIG. 6 is a graph showing results of the number of INFγ-producing cells in survivin 2B-specific mouse spleen cells in Example 54 and Comparative Example 30.
Figure 7:
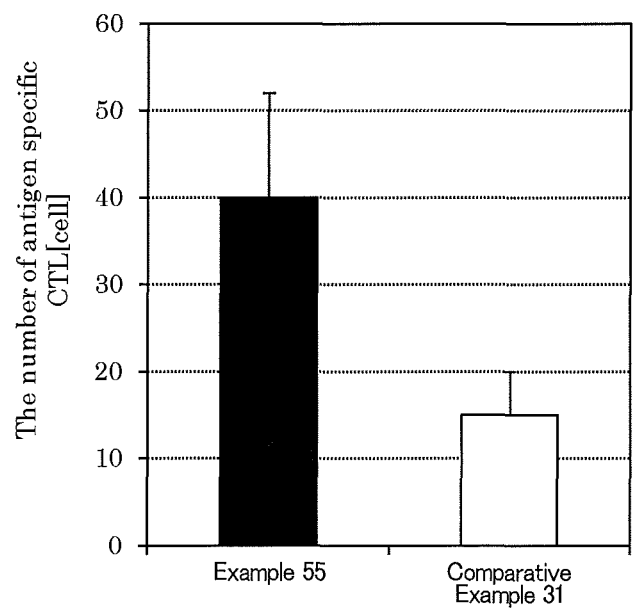
FIG. 7 is a graph showing results of the number of INFγ-producing cells in GPC3-specific mouse spleen cells in Example 55 and Comparative Example 31.
Figure 8:
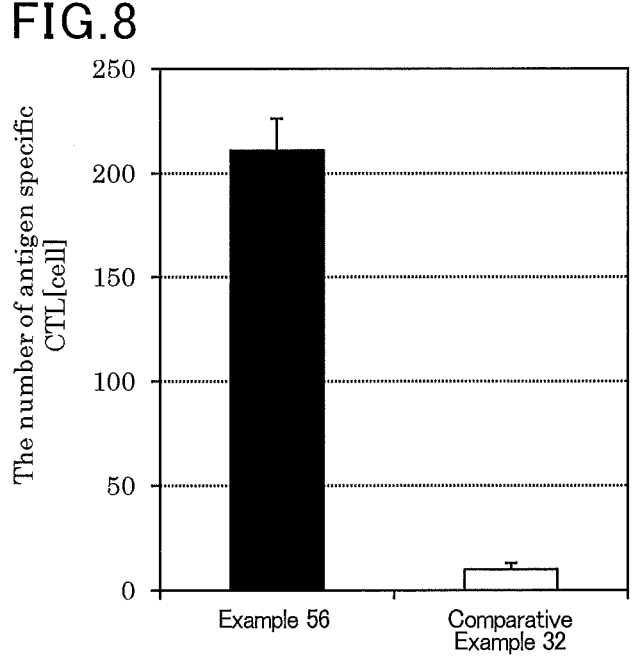
FIG. 8 is a graph showing results of the number of INFγ-producing cells in HER2/neu_A24-specific mouse spleen cells in Example 56 and Comparative Example 32.
Figure 9:
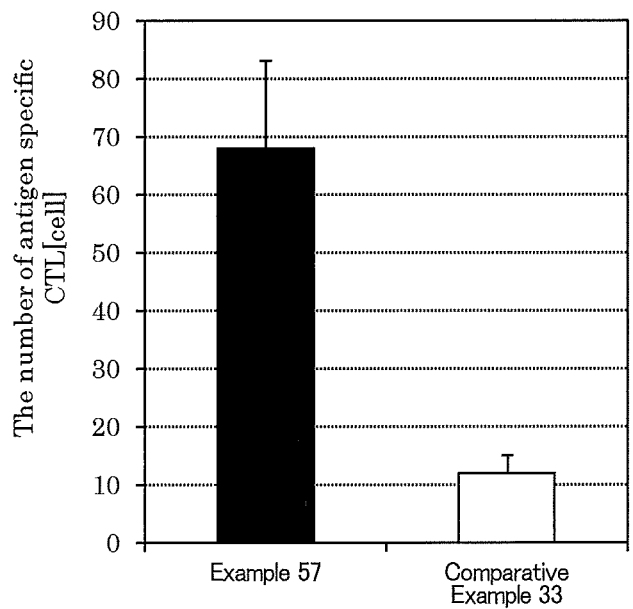
FIG. 9 is a graph showing results of the number of INFγ-producing cells in MAGE3_A24-specific mouse spleen cells in Example 57 and Comparative Example 33.
Figure 10:
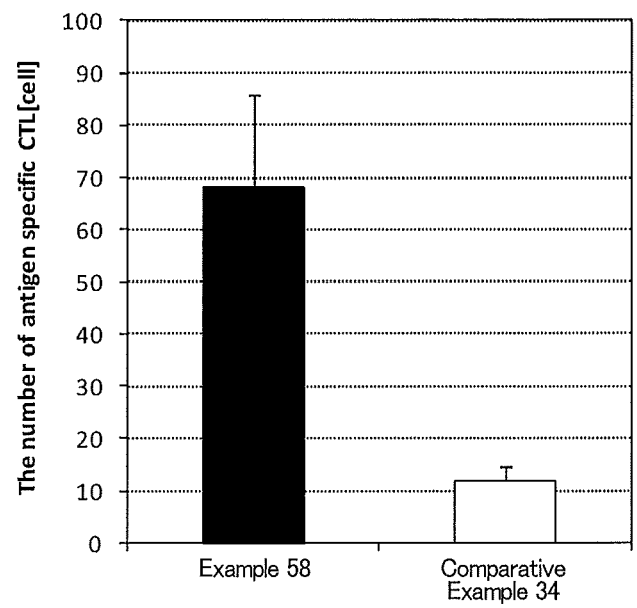
FIG. 10 is a graph showing results of the number of INFγ-producing cells in IPEP87-specific mouse spleen cells in Example 58 and Comparative Example 34.
Figure 11:
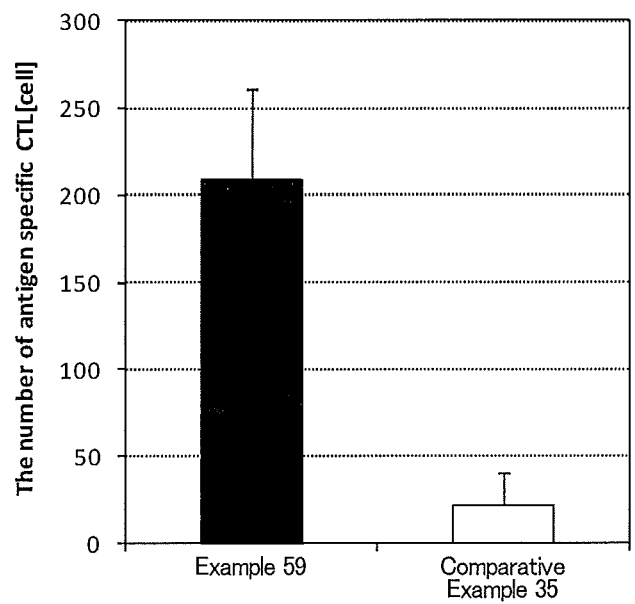
FIG. 11 is a graph showing results of the number of INFγ-producing cells in PR1-specific mouse spleen cells in Example 59 and Comparative Example 35.
Figure 12:
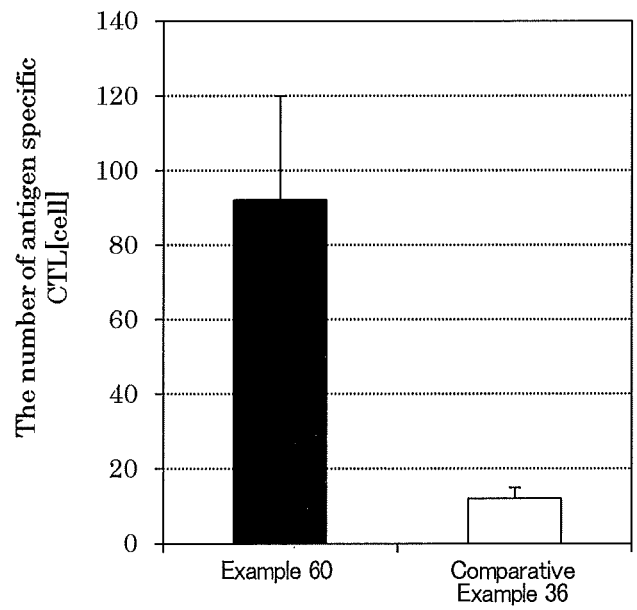
FIG. 12 is a graph showing results of the number of INFγ-producing cells in HER2/neu_A02-specific mouse spleen cells in Example 60 and Comparative Example 36.
Figure 13:
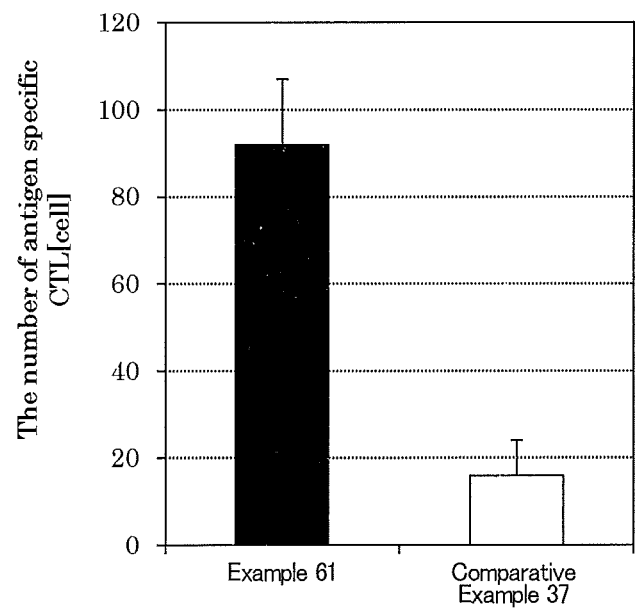
FIG. 13 is a graph showing results of the number of INFγ-producing cells in MAGE3_A02-specific mouse spleen cells in Example 61 and Comparative Example 37.
Figure 14:
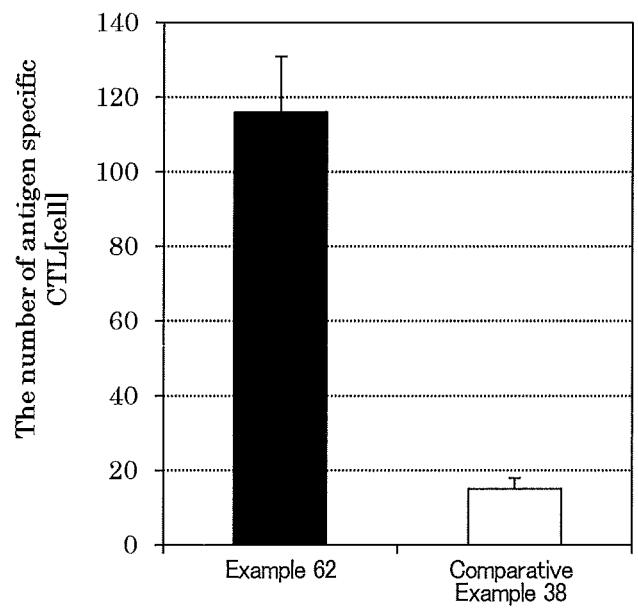
FIG. 14 is a graph showing results of the number of INFγ-producing cells in HBVenv-specific mouse spleen cells in Example 62 and Comparative Example 38.
Figure 15:
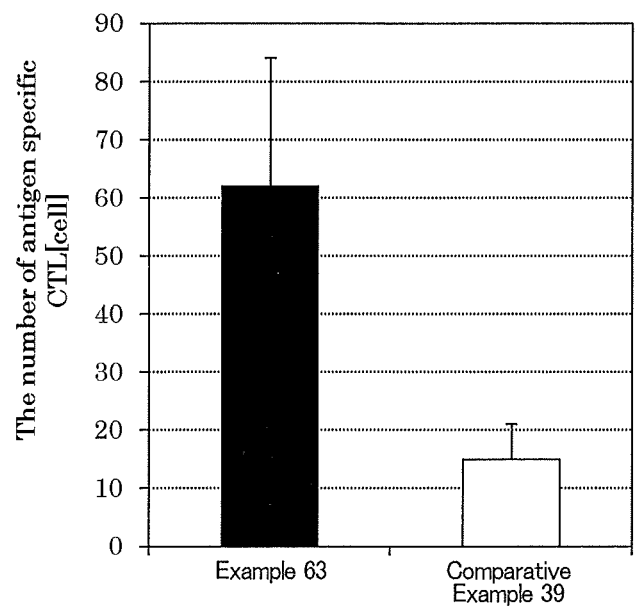
FIG. 15 is a graph showing results of the number of INFγ-producing cells in MUC1-specific mouse spleen cells in Example 63 and Comparative Example 39.

As shown in FIGS. 1 to 4, in examples, influenza HA-specific IgG which is humoral immunity was produced at high level. On the other hand, in comparative examples, the production amount of influenza HA-specific IgG was low. Also as shown in FIGS. 5 to 15, in examples, the antigen peptide-specific immune response increased, revealing that the cellular immunity is efficiently induced. In comparative examples, immune response little occurred.

These results reveal that using both an antigen, and a specific lipopolysaccharide derived from a gram-negative bacterium or a salt thereof as an adjuvant is effective for safe and effective induction of the systemic immunity.

INDUSTRIAL APPLICABILITY

The injectable vaccine composition of the present invention can effectively induce the systemic immune response because it contains the aforementioned specific adjuvant together with at least one antigen.

The invention claimed is:

1. An injectable vaccine composition to be administered by injection to a human being or an animal, comprising:
   at least one antigen, and
   as an adjuvant, a lipopolysaccharide from at least one gram negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas,* and *Enterobacter*, or a salt of the lipopolysaccharide;
   wherein a mass ratio between the adjuvant and the antigen (total mass of the adjuvant/total mass of the antigen) is 0.002 to 50.

2. The injectable vaccine composition according to claim 1, wherein the antigen is an infectious pathogen, an antigen from an infectious pathogen, or a cancer antigen.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Homo sapiens

<400> SEQUENCE: 1

Ala Tyr Ala Cys Asn Thr Ser Thr Leu
1               5

<210> SEQ ID NO 2
<211> LENGTH: 9

```
<212> TYPE: PRT
<213> ORGANISM: Homo sapiens

<400> SEQUENCE: 2

Glu Tyr Ile Leu Ser Leu Glu Glu Leu
1               5

<210> SEQ ID NO 3
<211> LENGTH: 9
<212> TYPE: PRT
<213> ORGANISM: Homo sapiens

<400> SEQUENCE: 3

Thr Tyr Leu Pro Thr Asn Ala Ser Leu
1               5

<210> SEQ ID NO 4
<211> LENGTH: 9
<212> TYPE: PRT
<213> ORGANISM: Homo sapiens

<400> SEQUENCE: 4

Ile Met Pro Lys Ala Gly Leu Leu Ile
1               5

<210> SEQ ID NO 5
<211> LENGTH: 9
<212> TYPE: PRT
<213> ORGANISM: Hepatitis C virus

<400> SEQUENCE: 5

Asp Leu Met Gly Tyr Ile Pro Ala Val
1               5

<210> SEQ ID NO 6
<211> LENGTH: 9
<212> TYPE: PRT
<213> ORGANISM: Homo sapiens

<400> SEQUENCE: 6

Val Leu Gln Glu Leu Asn Val Thr Val
1               5

<210> SEQ ID NO 7
<211> LENGTH: 9
<212> TYPE: PRT
<213> ORGANISM: Homo sapiens

<400> SEQUENCE: 7

Lys Val Phe Gly Ser Leu Ala Phe Val
1               5

<210> SEQ ID NO 8
<211> LENGTH: 9
<212> TYPE: PRT
<213> ORGANISM: Homo sapiens

<400> SEQUENCE: 8

Lys Val Ala Glu Ile Val His Phe Leu
1               5

<210> SEQ ID NO 9
<211> LENGTH: 9
<212> TYPE: PRT
<213> ORGANISM: Hepatitis B virus
```

```
<400> SEQUENCE: 9

Trp Leu Ser Leu Leu Val Pro Phe Val
1               5

<210> SEQ ID NO 10
<211> LENGTH: 9
<212> TYPE: PRT
<213> ORGANISM: Homo sapiens

<400> SEQUENCE: 10

Lys Ile Phe Gly Ser Leu Ala Phe Leu
1               5

<210> SEQ ID NO 11
<211> LENGTH: 9
<212> TYPE: PRT
<213> ORGANISM: Homo sapiens

<400> SEQUENCE: 11

Ser Thr Ala Pro Pro Val His Asn Val
1               5
```